United States Patent [19]

Braden et al.

[11] Patent Number: 5,298,146

[45] Date of Patent: Mar. 29, 1994

[54] DEVICE FOR THE SIMULTANEOUS DETECTION OF DISSIMILAR GAS COMPONENTS

[75] Inventors: Christoph Braden, Cologne; Jacques Deprez, Frechen, both of Fed. Rep. of Germany

[73] Assignee: Bayer Aktiengesellschaft, Leverkusen, Fed. Rep. of Germany

[21] Appl. No.: 966,229

[22] Filed: Oct. 26, 1992

[30] Foreign Application Priority Data

Nov. 8, 1991 [DE] Fed. Rep. of Germany ....... 4136779

[51] Int. Cl.$^5$ ............................................. G01N 27/26
[52] U.S. Cl. ..................................... 204/406; 204/407;
204/412; 204/415; 204/431; 204/432;
422/82.03; 422/82.04
[58] Field of Search ............... 204/406, 407, 412, 415,
204/431, 432; 422/82.03, 82.04

[56] References Cited

U.S. PATENT DOCUMENTS 4,506,226  3/1985  Luce et al. ............................ 204/406
4,729,824  3/1988  Giner .................................... 204/406

*Primary Examiner*—John Niebling
*Assistant Examiner*—Bruce F. Bell
*Attorney, Agent, or Firm*—Sprung Horn Kramer & Woods

[57] ABSTRACT

The device for the simultaneous detection of dissimilar gas components contains a number of electrochemical, three-electrode measuring cells with a common electrolyte, that are formed from a number of working electrodes with a common counter-electrode and a common reference electrode. Measured values are generated with the aid of a potentiostatic evaluation circuit that also adjusts and sets the potentials at the working electrodes. The current signals correlated with the gas concentrations to be measured are displayed with the aid of current-measuring instruments $11_1 \ldots 11_n$ in the lines to the working electrodes $5_1 \ldots 5_n$. At the same time it is important that all three-electrode measuring cells have a common counter-electrode 3 and a common reference electrode 4, and that the potentiostatic evaluation circuit 6 contains control loops $7_1 \ldots 7_n$ which maintain the potentials of the working electrodes $5_1 \ldots 5_n$ constant with respect to the reference electrode 4, both individually and independently of each other.

7 Claims, 7 Drawing Sheets

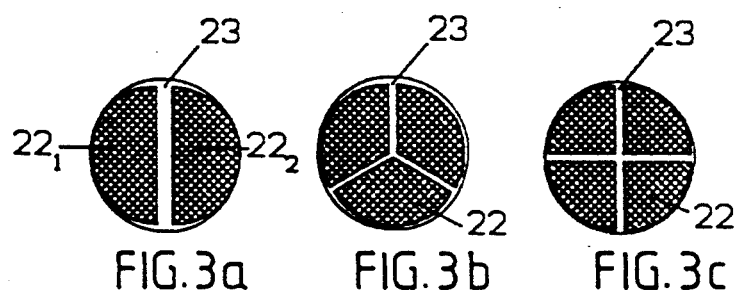
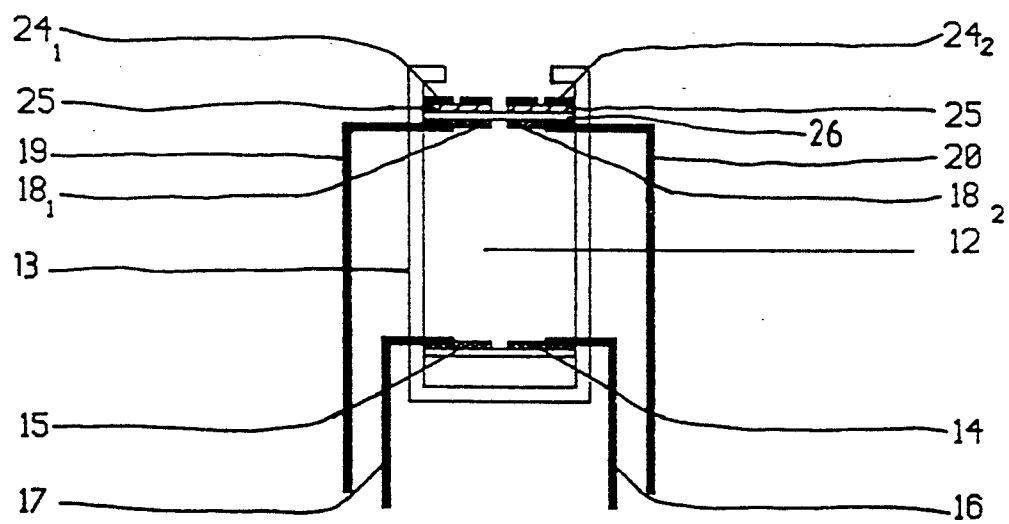
FIG. 2

DEVICE FOR THE SIMULTANEOUS DETECTION OF DISSIMILAR GAS COMPONENTS

BACKGROUND OF THE INVENTION

The invention is based on device for simultaneous detection of dissimilar gas components, with a number of electrochemical, three-electrode measuring cells (working electrode/counter-electrode/reference electrode) with a common electrolyte and a potentiostatic evaluation circuit for setting and regulating different potentials at the working electrodes, and for measuring the electrochemically-produced electric currents that are correlated with the individual gas concentrations.

Potentiostatic, three-electrode sensors are widely used for the measurement of gases in trace detection through to investigations on pure gases. These gas sensors are usually reproducible, sensitive, and can be made for a number of different gases. The selectivity can be controlled by the choice of catalyst at the measuring electrode, the electrolyte and the potential at the measuring electrode (working electrode). However, not all cross-sensitivities can be eliminated simultaneously. In fact, in practice a compromise has to be found between sensitivity and the suppression of cross-sensitivity with respect to other interfering gases.

Alternatively, several sensors can be combined in a sensor array and the various sensitivities for the sought-for measured components, and the interfering cross-components, are used during processing of the measured variables. The composition of the gas can then be determined (sample detection) by taking all sensor signals into account. In the past such sensor arrays have been based on conductivity-type solid-state gas sensors.

An electrochemical multi-electrode sensor in which the gas flows through successive electrochemical measuring cells, is described in DE 24 35 813. The measuring cells are interconnected via a resistance network that is connected to the electrodes, so that only one measuring voltage related to one specific pollutant is generated in each cell. This requires that a complete reaction takes place in each stage so that longer retention times and thus longer dead times have to be accepted during the measurement. Furthermore, the underlying measurement principle requires that all electrodes are brought out separately for each measuring cell. These characteristics contradict the requirement for a compact electrochemical, multi-electrode of simple construction. Temperature-differences and differing inflow rates in the individual measuring cells must also be taken into account.

Furthermore, potentiostatic, four-electrode sensors for measuring special gas systems are known from U.S. Pat. No. 4,315,753 and Ep 00 64 337. But there is no facility for selecting the potentials of the working electrodes independently of each other. Consequently there is very little freedom for optimizing the selectivities individually. Apart from that, expensive gas control is also necessary to some extent in this state-of-the-art.

The aim of the invention is to measure several gas components simultaneously and independently of each other with the aid of an electrochemical, multi-electrode sensor, whereby with regard to optimization of the selectivity for detection of the individual gas components, full freedom in determining the electrode potential, the choice of electrode material, including catalytic additives, and the use of suitable gas filters and gas diffusion barriers, is provided.

SUMMARY OF THE INVENTION

According to the invention this aim is achieved in an electrochemical sensor with a number of three-electrode measuring cells in that a) the three-electrode measuring cells are formed by a number of working electrodes with a common counter-electrode and a common reference electrode, which are in contact with the same electrolyte, b) a potentiostatic evaluation circuit contains control loops that maintain the potentials of the working electrode constant with respect to the reference electrode, both individually and independently of each other, c) and that the evaluation circuit contains means for detecting the electric current signals correlated to the gas concentrations, which are flowing in the working electrodes.

For preference, each control loop in the potentiostatic evaluation circuit consists of two operational amplifiers connected in cascade, whereby the potential-difference between one working electrode and the common reference electrode is fed via a high-resistance tapping point on the first amplifier and the second amplifier compares this potential-difference at the output of the first amplifier with a preset set-point $U_n$ and adjusts the current $I_n$ flowing from the output of the second amplifier to the working electrode so as to minimize the deviation from the set-point $U_n$. The currents $I_n$ which appear at the various working electrodes during this adjustment are the measured values of the gas concentrations of the gas components arriving at the working electrodes.

A fluid electrolyte is used for preference. The working electrodes are advantageously positioned on the one surface of the electrolyte in the form of physically-separate measuring fields, whereas the common counter-electrode and the common reference electrode are arranged on the opposite side of the electrolyte. A compact, electrochemical, multi-electrode sensor can be produced in this way very satisfactorily.

The sensitivity of a working electrode for a specific gas, and thus the sensitivity of a measuring field for a particular gas component, depends, in the well-known manner, on the electrode material and the electrode potential and can thus be adjusted via the electrode potential. Furthermore, the selectivity of a measuring field can be improved by catalytic activation of the working electrode and by connecting gas-specific filters on the input side. In addition, the sensitivity of a measuring cell can be varied either by orifices or diffusion membranes. In principle, a multi-electrode sensor with different sensitivities for the measuring fields permits sample detection and thus the identification of certain gas mixtures.

The following advantages are obtained with the invention:

Due to the compact form of construction, a distinct reduction in volume can be achieved compared to the previously-known electrochemical, multi-electrode sensors, since all working electrodes use the same reference electrode, counter-electrode, electrolyte and complete sensor housing.

A further reduction in volume results from the use of a solid-state electrolyte when the sensor is manufactured using hybrid technology.

All working electrodes are operated at identical temperature, pressure and flow conditions. Interference effects which can be attributed to fluctuations in these parameters can be avoided in this way.

All measuring signals at the working electrodes (working electrode currents $I_n$) are referred to the same reference electrode and the same electrolyte so that drift in the reference electrode potential can be detected and compensated if necessary.

With the multi-electrode sensor according to the invention, a very high-resolution (depending on the number of working electrodes), cyclical voltametric plot (voltamogram) can be statically recorded instantaneously and simultaneously, whereas in classical, cyclical voltametry only dynamic limiting values are obtained, even with very slow measurements (rates of up to 1 mV/min.)

Furthermore, the multi-electrode sensor according to the invention permits specific suppression of cross-sensitivities with respect to other undesirable gas components.

Since the individual working electrodes are operated potentiostatically and completely independently of each other, there is complete freedom in the choice and adjustment of the electrode potential, the choice of catalysts at the working electrodes, the series-connection of gas-specific filters, so that the individual measuring cells can be matched to the measurement problem with optimum selectivity.

The gas under investigation appears simultaneously at all working electrodes since the gas paths are identical. As a result, different response times which can be attributed to different flow paths or diffusion distances in the individual gas components, can be avoided.

In the multi-electrode sensor according to the invention in principle there are no limitations with regard to the detection of specific gas components or a specific mixture. So solid, fluid, inorganic or organic electrolytes can be used, for example.

A practical example of the invention is described below with the aid of drawings in which:

FIG. 2 shows the practical construction of a multi-electrode sensor.

FIGS. 3a–3c show versions of the multi-electrode sensor with two, three and four measuring fields on the gas side of a fluid electrolyte.

DETAILED DESCRIPTION OF THE INVENTION

Figure 1:
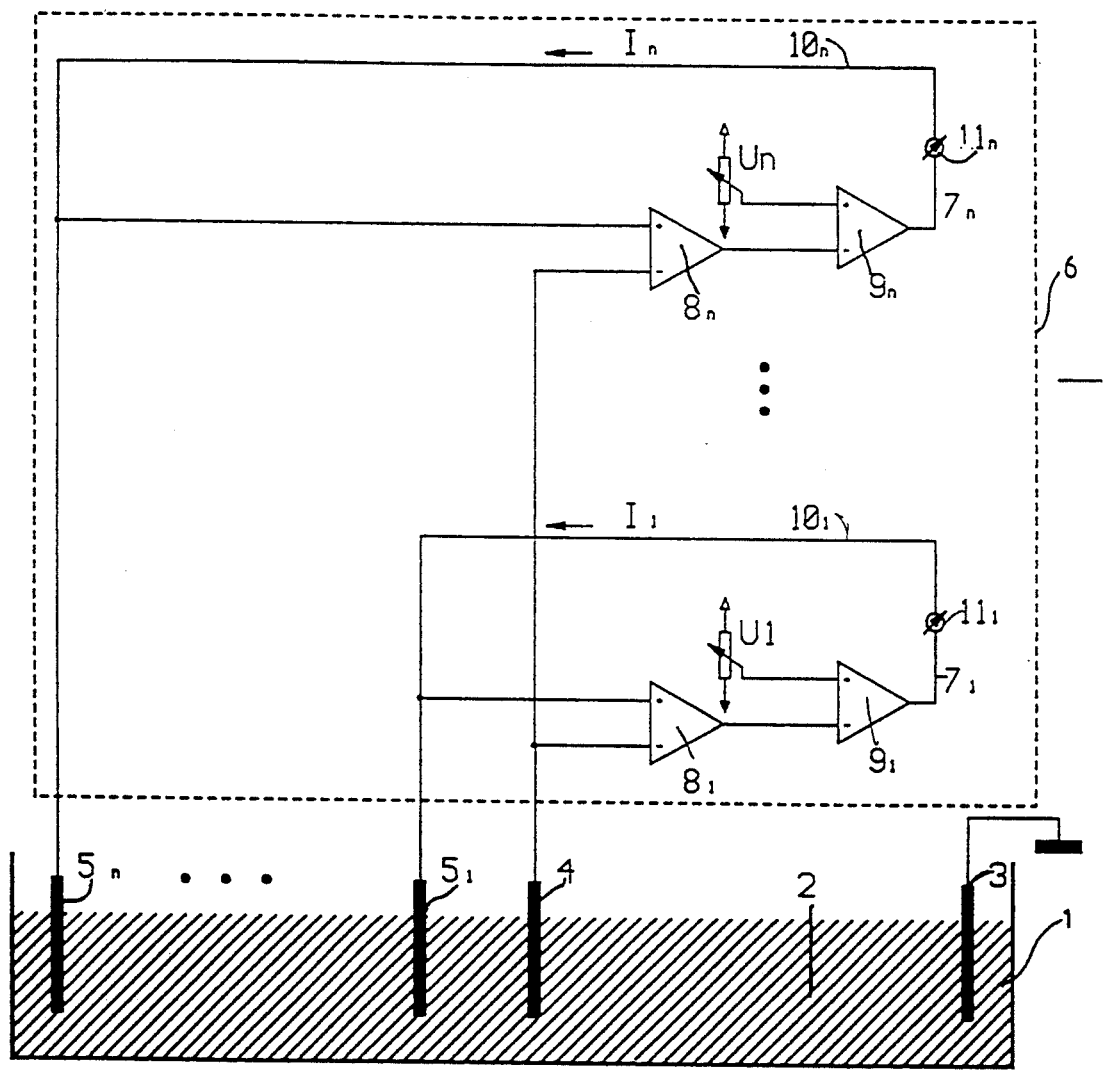
FIG. 1 shows the basic construction of a multi-electrode sensor with a multi-potentiostatic circuit for controlling the working electrodes, potentials and measurement of the currents flowing in the working electrodes.

In FIG. 1 the multi-electrode sensor with the housing 1, the measuring cell electrolyte 2 and the electrodes is shown only schematically. The counter-electrode 3, the reference electrode and the working electrodes $5_1 \ldots 5_n$ are immersed in the electrolyte 2. Up to eight working electrodes (n=8) can be provided Here each working electrode $5_n$ forms a three-electrode sensor with the common counter-electrode 3 and the common reference electrode 2.

The evaluation circuit 6 consists of n potentiostatic control loops $7_1 \ldots 7_n$ coupled together via the common electrodes 3 and 4. Each control loop consists of two operational amplifiers $8_n$ and $9_n$ connected in cascade. A high-resistance measurement of the potential-difference between a working electrode $5_n$ and the common reference electrode 4 is made by means of the first amplifier $8_n$. This difference is compared at the output of the first amplifier $8_n$ with the respective set-point $U_n$ by the second amplifier $9_n$ and the current through the feedback line $10_n$ leading to the working electrode $5_n$ is adjusted automatically so as to minimize the deviation from the set-point $U_n$ (control deviation). The set-points $U_n$ and thus the potentials at the working electrodes $5_n$ can be set individually and independently of each other. The currents $I_n$ through the feedback lines $10_n$ flow from the working electrodes $5_n$ through the electrolyte 2 to the common, earthed counter-electrode 3. Since the measurement of the potentials between the working electrodes $5_n$ and the common reference electrode 4 is a high-resistance one, and the common counter-electrode 3 is earthed, the individual potentiostatic stages $7_n$ (potentiostatic control loops) operate independently of each other. The currents $I_1 \ldots I_n$ measured with the indicating instruments $11_1 \ldots 11_n$ in the feedback lines $10_1 \ldots 10_n$ are a direct measurement of the gas volumes converted at the working electrodes $5_1 \ldots 5_n$. Other means for recording the currents flowing in the working electrodes $5_1 \ldots 5_n$, e.g. electronic memories, can also be used in place of the indicating instruments $11_1 \ldots 11_n$. Here the gas being measured is fed simultaneously to all working electrodes $5_1 \ldots 5_n$.

FIG. 2 shows the practical construction of an electrochemical, multi-electrode sensor. In this case the electrolyte 12 consists of an aqueous electrolyte solution (50% $H_2SO_4$) that is enclosed by the container 13. The lower end is bounded by the counter-electrode 14 and the reference electrode 15 (e.g. a Pt/air electrode). The counter-electrode 114 and the reference electrode 15 are brought out via the connections 16, 17.

Two working electrodes $18_1$ and $18_2$ that are connected to the supply leads 19 and 20 are arranged at the upper end.

The working electrodes are provided with a diffusion membrane 26, i.e. on the gas side. A gas-permeable spacer 25 on which orifices $24_1$ and $24_2$ for adjusting and matching the sensitivity are arranged, is placed above the diffusion membrane 26, which consists of a PTFE film, for example. The inner face of the working electrodes $18_1$, $18_2$, that is in contact with the electrolyte 12 can be activated catalytically. The choice of suitable catalysts to selectively influence the electrochemical reaction at the working electrode/electrolyte boundary surface is state-of-the-art. The sensitivity of the multi-electrode sensor can be matched to the respective measurement task with the aid of a series-connected orifice 21.

As shown in FIG. 3a, semicircular measuring fields $22_1$ and $22_2$ separated from each other by a gap 23 are formed by the working electrodes $18_1$ and $18_2$ on the surface of the electrolyte 12. FIGS. 3b and 3c show practical examples of a sensor surface with three or four sector-shaped measuring fields, respectively, for different gas components. To improve the selectivity, different gas-specific filters can be connected in series with the measuring fields. The sensor design as shown in FIGS. 2 and 3 facilitates a space-saving and compact multi-electrode sensor construction.

EXAMPLE 1

Figure 4:
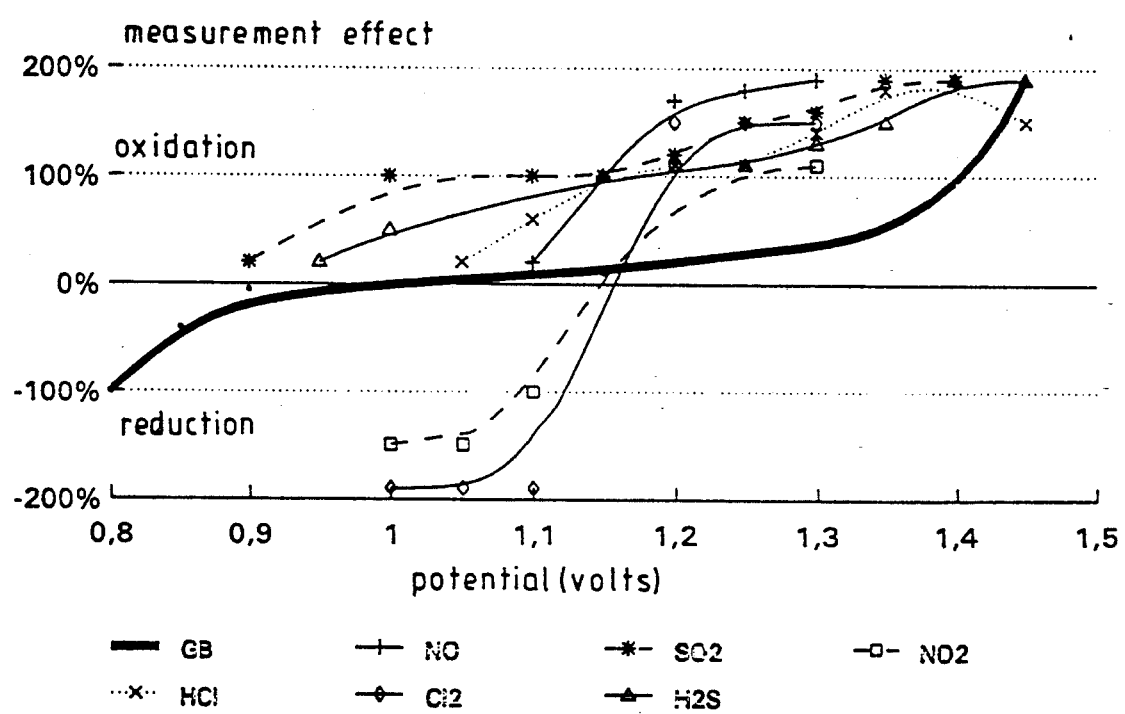
FIG. 4–6 show examples of different measurements to explain the effect of the working electrode potential on the selectivity.

The $Au/H_2SO_4$ system is described as an example, for which FIG. 4 shows the potential-dependent sensitivity for the measurement of various gases, using classical, cyclical voltametry. A PTFE-gold powder, gas diffusion electrode is used. The electrolyte consists of 0,5 m (mol/l) sulphuric acid. The measurements are carried out at room temperature and at a test gas flow-rate of 5 l/h. The graph shows quasi-stationary current/voltage curves for the gas components No. $SO_2$, $NO_2$, HCl, $Cl_2$ and $H_2S$. The so-called basic trace (thick curve) is recorded with pure air. The potential is measured with respect to a reversible $H_2$ electrode in the electrolyte. A reasonable gas-specific electrode potential can be determined each time from this graph—measured by means of a standard three-electrode sensor. When setting the potential, a compromise is usually made between the desired sensitivity and the cross-sensitivities to be suppressed. The multi-electrode sensor according to the invention creates the conditions whereby individual working electrodes are always operated at the most favourable potentials. For example, the potentials are set to 1.2V for the NO measurement, 1.1V for the $SO_2$ measurement and 1V for the $NO_2$ measurement. Since experience shows that the measurement sensitivity is sufficiently high for all test components, this means that the loss of sensitivity caused by reducing the measuring electrode surface in accordance with the measuring fields 22, (FIG. 3a–3c) is no limitation. The measured currents can be used for direct verification of the individually-detected gases. Furthermore, the cross-sensitivity of one or more main components can be corrected arithmetically by measuring several components in parallel.

EXAMPLE 2

Figure 5:
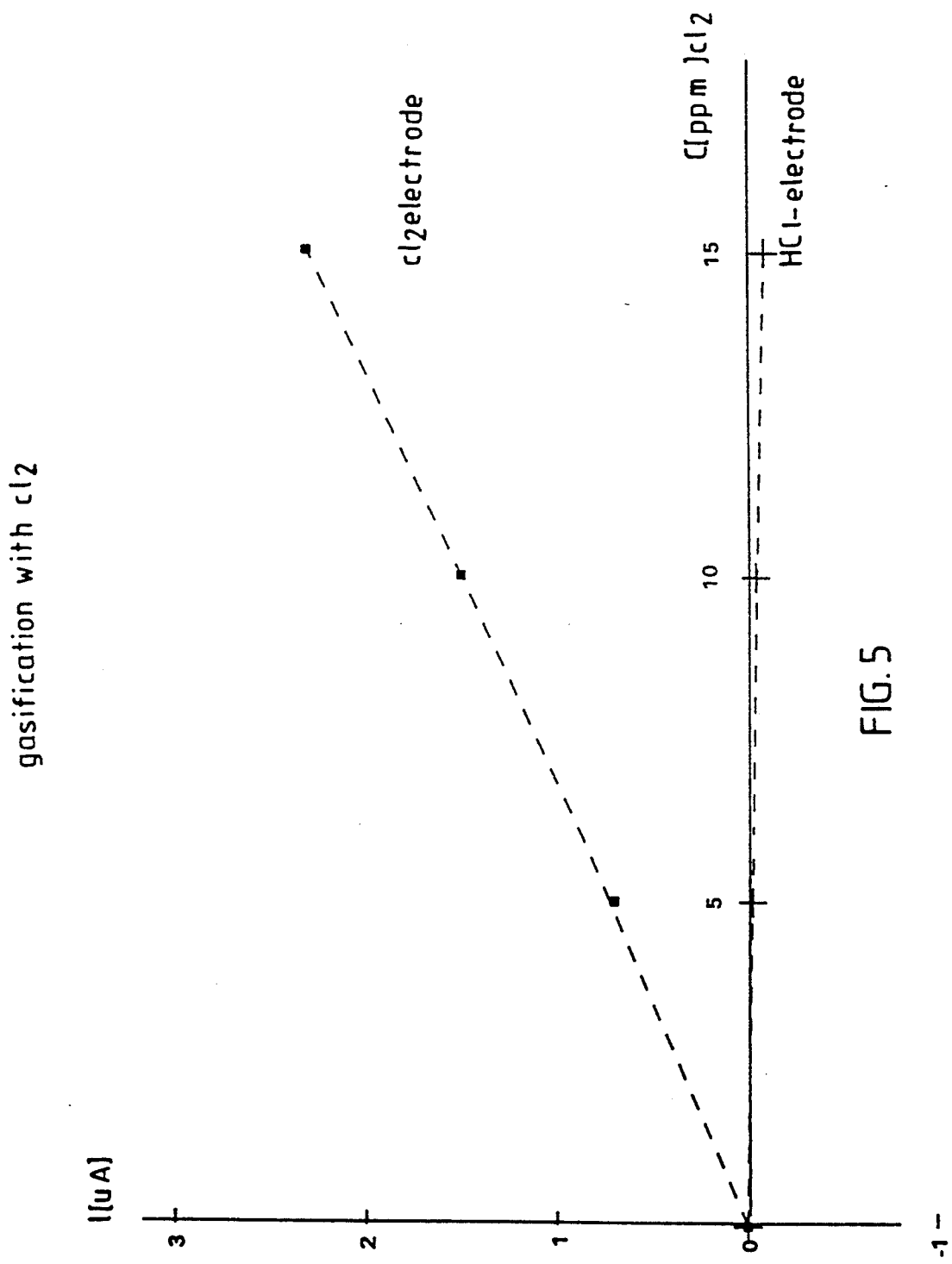
Figure 6:
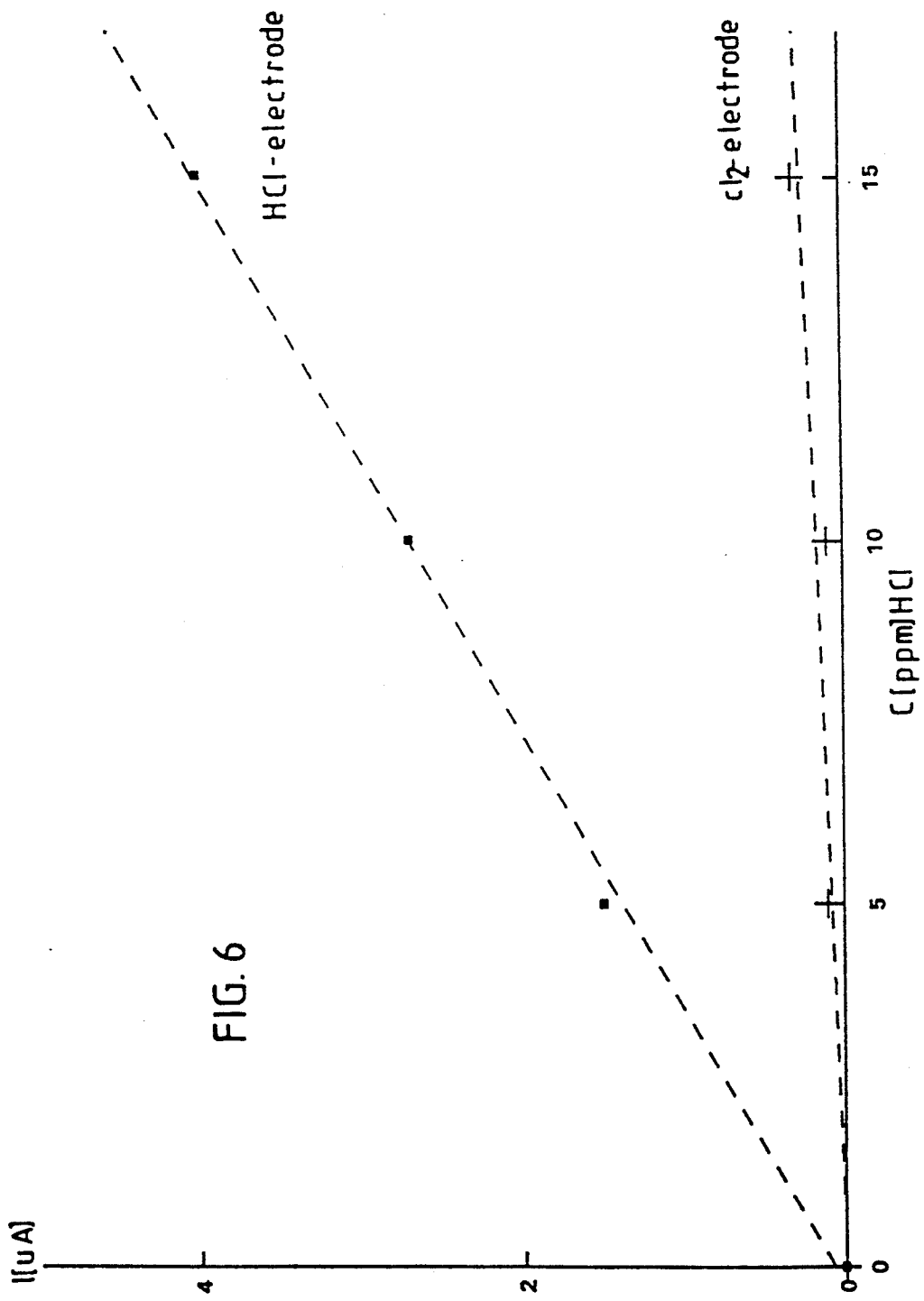

FIG. 5 shows the variation in the measuring currents in a specified HCl concentration for a multi-electrode sensor with only two working electrodes. Both working electrodes consist of gold. The first working electrode is operated at a potential of 150 mV and the second working electrode at 0 mV with respect to a Pt/air electrode in a sulphuric acid electrolyte. It is known that the first working electrode reacts more sensitively to HCl. FIG. 5 shows the measuring currents of the same multi-electrode sensor in relation to a fixed $Cl_2$ concentration. Due to the different working electrode potentials, in this case the second working electrode exhibits a higher sensitivity to $Cl_2$ than the first working electrode.

The selectivity can be increased in the known manner so that materials with catalytic action can be used as working electrodes. For example, a sensor for the simultaneous and independent measurement of $NO_2$ and CO can be produced with the aid of a ruthenium black working electrode that is operated at an electrode potential of 0.6V with respect to the reversible hydrogen electrode, under a platinum working electrode set to a potential of 1.1V, and with sulphuric acid as electrolyte.

EXAMPLE 3

As the last example, the time characteristic and the cross-sensitivity of a multi-electrode sensor shown in FIG. 1 was examined for the gases $CL_2$ and HCl. Here the two working electrodes consist of gold powder diffusion electrodes. Platinum black diffusion electrodes were used as the reference and counter-electrodes. The electrolyte was 50% sulphuric acid.

Figure 7:
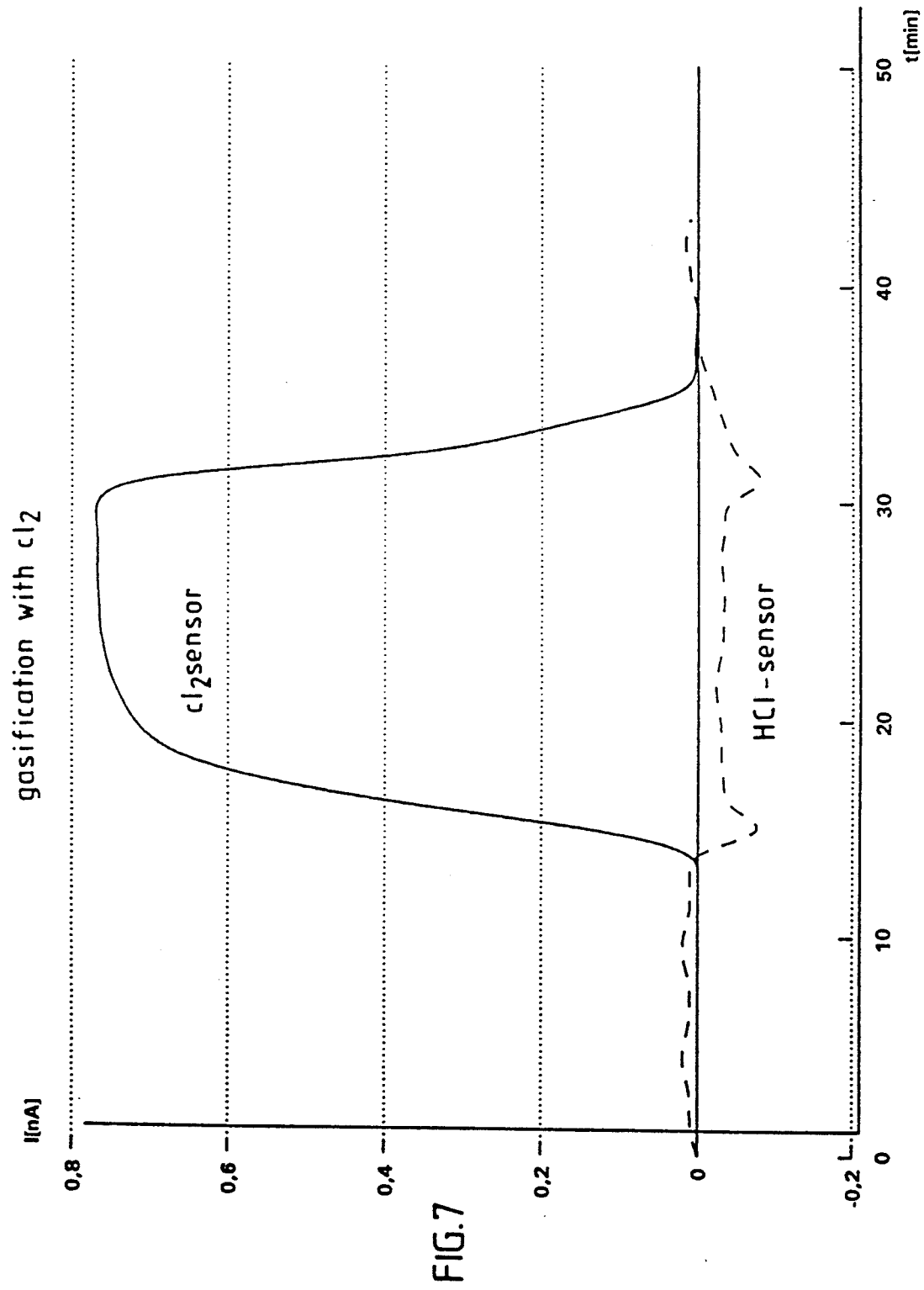
FIG. 7–8 shows the time characteristic of the measuring signal (response curve) at two measuring fields in a multi-electrode sensor in FIG. 1 when gasified with $Cl_2$ and HCl.

The potential for the chlorine-sensitive working electrode was set to 1000 mV and 1150 mV for the HCl-sensitive working electrode. The curves of the measuring signals plotted simultaneously with respect to time at the $CL_2$ working electrode and the HCl working electrode when the multi-electrode sensor was gasified at 5 ppm $CL_2$, the test gas being supplied at a flow-rate of 5 l/h, are shown in FIG. 7. The $CL_2$ working electrode shows a significant measuring signal, whereas the HCl working electrode has only a low cross-sensitivity.

Figure 8:
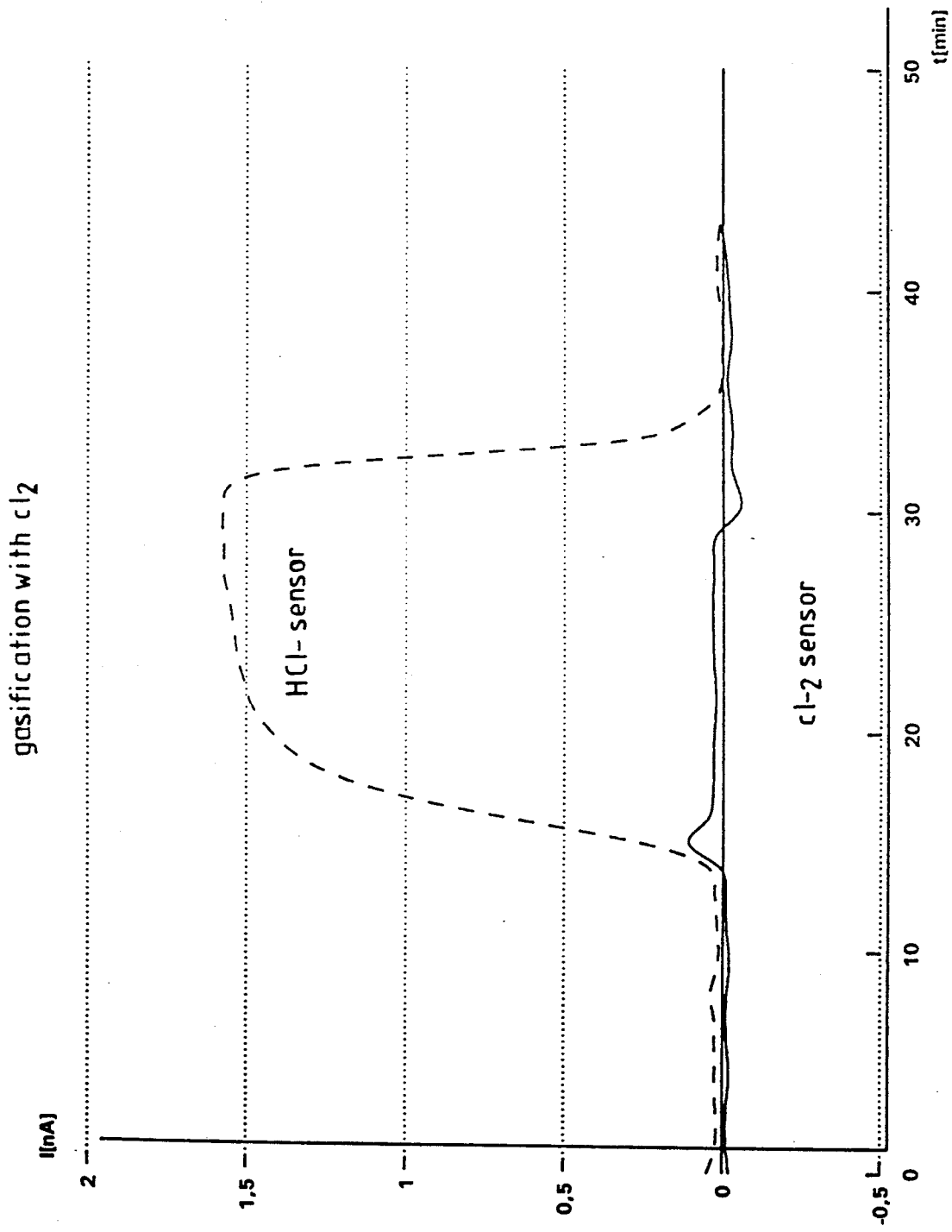

Similarly, FIG. 8 shows the response curves for HCl gasification of the same multi-electrode sensor. Incidentally, the conditions are identical to those in the test in FIG. 7. In this case the HCl working electrode exhibits a significant measuring signal, whilst conversely, the $Cl_2$ working electrode has a low cross-sensitivity.

We claim:
1. A device for the simultaneous detection of dissimilar gas components, comprising:
   a. at least two three-electrode measuring cells, wherein each measuring cell comprises one working electrode, one counter-electrode and one referenced electrode and wherein the at least two measuring cells having a common counter-electrode, a common reference electrode and the working electrodes all in a common electrolyte;
   b. A potentiostatic evaluation circuit comprising a separate control loop for each cell for maintaining a constant potential across each working electrode with respect to the reference electrode, the constant potential of one working electrode being individual and independent of the constant potential across other working electrodes; and
   c. wherein the evaluation circuit further comprises means for separately detecting electric current flowing in each working electrode, each current corresponding to a gas concentration of a different gas component.

2. The device according to claim 1, wherein each control loop comprises a first operational amplifier effecting a high resistance measurement of the potential difference between an associated working electrode and the reference electrode, a second operational amplifier connected in series with the first operational amplifier for comparing the potential difference to a preset setpoint voltage and means for adjusting a current output from the second operational amplifier to minimize any difference from the comparison.

3. The device according to claim 1, wherein the electrolyte comprises an electrolyte solution and wherein the working electrodes delimit the electrolyte on a gas side thereof and comprises physically separate measuring fields on a common membrane and wherein the counter-electrode and reference electrode are disposed on an opposite side of the electrolyte.

4. The device according to claim 3, further comprising gas specific filters connected in series with the measuring fields.

5. The device according to claim 3, wherein the working electrodes comprise catalysts.

6. The device according to claim 3, further comprising orifices or diffusion membranes in series with the working electrodes for adjusting the sensitivity thereof.

7. The device according to claim 1, for the measurement of HCl and Cl, wherein the electrolyte consists of aqueous sulphuric acid and the working electrodes consist of gold.

* * * * *